United States Patent
Patil et al.

(10) Patent No.: US 10,501,393 B2
(45) Date of Patent: Dec. 10, 2019

(54) PROCESSES FOR PREPARING VINYLIDENE DIMER DERIVATIVES

(71) Applicant: ExxonMobil Research and Engineering Company, Annandale, NJ (US)

(72) Inventors: Abhimanyu O. Patil, Westfield, NJ (US); Satish Bodige, Wayne, NJ (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 156 days.

(21) Appl. No.: 15/685,172

(22) Filed: Aug. 24, 2017

(65) Prior Publication Data

US 2018/0086682 A1    Mar. 29, 2018

Related U.S. Application Data

(60) Provisional application No. 62/400,248, filed on Sep. 27, 2016.

(51) Int. Cl.
 C07C 29/38 (2006.01)
 C07C 33/025 (2006.01)
 (Continued)

(52) U.S. Cl.
 CPC ............ *C07C 29/38* (2013.01); *C07C 29/44* (2013.01); *C07C 33/025* (2013.01); *C07C 67/08* (2013.01);
 (Continued)

(58) Field of Classification Search
 CPC ....... C07C 29/38; C07C 29/44; C07C 33/025; C07C 67/08; C07C 69/24; C10M 105/12;
 (Continued)

(56) References Cited

U.S. PATENT DOCUMENTS

| 3,887,624 A | 6/1975 | Gipson et al. |
| 5,001,180 A * | 3/1991 | Lundy .................... C08K 5/101 524/311 |

(Continued)

FOREIGN PATENT DOCUMENTS

| JP | 2005298443 A | 10/2005 |
| WO | 2007144473 A1 | 12/2007 |

OTHER PUBLICATIONS

Okachi et al., "Practical Carbonyl-Ene Reactions of α-Methylstyrenes with Paraformaldehyde Promoted by a Combined System of Boron Trifluoride and Molecular Sieves 4A", Organic Letters, Apr. 25, 2002, pp. 1667-1669, vol. 4 (10), ACS Publications.

(Continued)

*Primary Examiner* — James C Goloboy
(74) *Attorney, Agent, or Firm* — Priya G. Prasad (57) ABSTRACT

This disclosure provides a process for producing vinylidene dimer derivatives by subjecting one or more vinylidene dimers and one or more carbonyl-containing compounds to a carbonyl-ene reaction, optionally in the presence of a catalyst, to produce one or more vinylidene dimer derived alcohols. This disclosure also provides a process for producing vinylidene dimer derivatives by reacting one or more vinylidene dimers with one or more carbonyl-containing compounds, optionally in the presence of a catalyst, to produce one or more vinylidene dimer derived alcohols. This disclosure further provides vinylidene dimer derivatives (e.g., vinylidene dimer derived alcohols and esters) produced by these processes. This disclosure still further provides for hydrogenating/reacting the vinylidene dimer derived alcohols with acids or anhydrides to produce vinylidene dimer derived esters. This disclosure yet further relates to lubricating ester oil base stocks, and lubricating oils containing the lubricating ester oil base stocks.

6 Claims, 2 Drawing Sheets

(51) Int. Cl.
  *C07C 69/24* (2006.01)
  *C10M 105/34* (2006.01)
  *C07C 29/44* (2006.01)
  *C07C 67/08* (2006.01)
  *C10M 105/12* (2006.01)
  *C10M 105/14* (2006.01)

(52) U.S. Cl.
  CPC ............ *C07C 69/24* (2013.01); *C10M 105/12* (2013.01); *C10M 105/14* (2013.01); *C10M 105/34* (2013.01); *C10M 2207/0215* (2013.01); *C10M 2207/0225* (2013.01); *C10M 2207/2815* (2013.01); *C10M 2207/2855* (2013.01)

(58) Field of Classification Search
  CPC .............. C10M 105/14; C10M 105/34; C10M 2207/0215; C10M 2207/0225; C10M 2207/2815; C10M 2207/2855
  See application file for complete search history.

(56) References Cited

U.S. PATENT DOCUMENTS

| | | | | |
|---|---|---|---|---|
| 5,286,397 | A | * | 2/1994 | Schmid ................ C10M 105/36 508/496 |
| 8,710,147 | B2 | * | 4/2014 | Cherpeck ................ C08F 8/00 525/154 |

OTHER PUBLICATIONS

Snider et al., "Dimethylaluminum Chloride Catalyzed Ene Reactions of Aldehydes", Journal of the American Chemical Society, Jan. 1982, pp. 555-563, vol. 104(2), ACS Publications.

Arnold et al., "Preparation and Reactions of Methylenecyclopentane", Journal of the American Chemical Society, Jul. 1950, pp. 2871-2873, vol. 72(7), ACS Publications.

Blomquist et al., "Thermal Condensation of formaldehyde with Acyclic Olefins 1", Journal of the American Chemical Society, Sep. 1, 1957, pp. 4972-4976, vol. 79(18), ACS Publications.

Kulkarni, et al., "Synthesis of Phytollsomers: 7, 11, 15-Trimethyl-3methylenehexadecanol & 3, 7, 11, 15-Tetramethylhexadec-3-en-1-01 & Their Conversion into Vitamin E", Indian Journal of Chemistry, 1988, pp. 65-66, vol. 27B.

Maruoka, et al., "Stabilization of Reactive Aldehydes by Complexation with Methylaluminium Bis (2, 6-diphenylphenoxide) and Their Synthetic Application", Journal of the American Chemical Society, 1993, pp. 3943-3949, vol. 115(10), ACS Publications.

Ramaswami et al., "Terpenoids. IL. The Prins reaction on the isopropylidene-type double bonds", The Journal of Organic Chemistry, Aug. 1, 1964, pp. 2245-2248, vol. 29, No. 8, ACS Publications.

International Search Report and Written Opinion PCT/US2017/048331 dated Nov. 10, 2017.

* cited by examiner

PROCESSES FOR PREPARING VINYLIDENE DIMER DERIVATIVES

CROSS-REFERENCE TO RELATED APPLICATIONS

This application claims the benefit of U.S. Provisional Application No. 62/400,248, filed on Sep. 27, 2016, the entire contents of which are incorporated herein by reference.

FIELD

This disclosure relates to processes for producing vinylidene dimer derivatives by subjecting a vinylidene dimer and a carbonyl-containing compound to a carbonyl-ene reaction. This disclosure also relates to vinylidene dimer derivatives (e.g., vinylidene dimer derived alcohols and esters) produced by these processes. This disclosure further relates to the synthesis of ester fluids based upon 'Guerbet type' branched alcohol prepared from vinylidene mPAO dimer chemistry. This disclosure still further relates to hydrogenating/reacting the vinylidene dimer derived alcohols with acids or anhydrides to produce vinylidene dimer derived esters. This disclosure yet further relates to lubricating ester oil base stocks, and lubricating oils containing the lubricating ester oil base stocks.

BACKGROUND

Currently Oxo or Guerbet alcohols are used to make various intermediate products. Generally short chain olefins, (e.g., C3 or C4) can be oligomerized to yield branched olefins with 2 or more branches per molecules. The branched olefins can then be hydroformylated to yield highly branched alcohols.

Such alcohols can be produced by commercial processes, for example, the Oxo or hydroformylation of long chain olefins. Typical long chain alcohols are the commercially available, for example, the Exxal™ alcohols available from ExxonMobil. ExxonMobil makes various Exxal™ alcohols that are isomeric mixtures of primary, branched aliphatic alcohols, with high alcohol purity. The grade slate ranges from C8 to C13 and includes Exxal™ 8 (isooctanol, alcohols C7-C9-iso, C8-rich), Exxal™ 9 (isononanol, alcohols C8-C10-iso, C9-rich), Exxal™ 10 (isodecanol, alcohols C9-C11-iso, C10-rich), Exxal™ 11 (isoundecanol, alcohols C9-C11-branched), and Exxal™ 13 (isotridecanol, alcohols C11-14-iso, C13-rich).

There is a need for an alternative to conventional branched alcohol process technology. In particular, there is a need for a new branched alcohol process technology in which the branched alcohols are useful in the synthesis of ester based low viscosity low volatility (LVLV) base stocks.

The present disclosure also provides many additional advantages, which shall become apparent as described below.

SUMMARY

This disclosure relates in part to a process for producing a composition comprising one or more vinylidene dimer derivatives. The process comprises subjecting one or more vinylidene dimers and one or more carbonyl-containing compounds to a carbonyl-ene reaction, optionally in the presence of a catalyst, under reaction conditions sufficient to produce one or more vinylidene dimer derived alcohols.

This disclosure also relates in part to a process for producing a composition comprising one or more vinylidene dimer derivatives. The process comprises: subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; reacting the one or more vinylidene dimer derived alcohols with one or more acids or anhydrides under reaction conditions sufficient to produce one or more vinylidene dimer derived unsaturated esters; and hydrogenating the one or more vinylidene dimer derived unsaturated esters under reaction conditions sufficient to produce one or more vinylidene dimer derived saturated esters.

This disclosure further relates in part to a process for producing a composition comprising one or more vinylidene dimer derivatives. The process comprises: subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated esters.

This disclosure yet further relates in part to a process for producing a composition comprising one or more vinylidene dimer derivatives. The process comprises reacting one or more vinylidene dimers with one or more carbonyl-containing compounds, optionally in the presence of a catalyst, under reaction conditions sufficient to produce one or more vinylidene dimer derived alcohols.

This disclosure also relates in part to a process for producing a composition comprising one or more vinylidene dimer derivatives. The process comprises reacting one or more vinylidene dimers with one or more carbonyl-containing compounds, optionally in the presence of a catalyst, under reaction conditions sufficient to produce one or more vinylidene dimer derived alcohols; reacting the one or more vinylidene dimer derived alcohols with one or more acids or anhydrides under reaction conditions sufficient to produce one or more vinylidene dimer derived unsaturated esters; and hydrogenating the one or more vinylidene dimer derived unsaturated esters under reaction conditions sufficient to produce one or more vinylidene dimer derived saturated esters.

This disclosure further relates in part to a process for producing a composition comprising one or more vinylidene dimer derivatives. The process comprises reacting one or more vinylidene dimers with one or more carbonyl-containing compounds, optionally in the presence of a catalyst, under reaction conditions sufficient to produce one or more vinylidene dimer derived alcohols; hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated esters.

This disclosure yet further relates in part to a composition comprising one or more vinylidene dimer derived alcohols. The one or more vinylidene dimer derived alcohols are prepared by a process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols.

This disclosure relates in part to a composition comprising one or more vinylidene dimer derived saturated esters. The one or more vinylidene dimer derived saturated esters are prepared by a process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; reacting the one or more vinylidene dimer derived alcohols with one or more acids or anhydrides under reaction conditions sufficient to produce one or more vinylidene dimer derived unsaturated esters; and hydrogenating the one or more vinylidene dimer derived unsaturated esters under reaction conditions sufficient to produce one or more vinylidene dimer derived saturated esters.

This disclosure also relates in part to a composition comprising one or more vinylidene dimer derived saturated esters. The one or more vinylidene dimer derived saturated esters are prepared by a process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated esters.

This disclosure further relates in part to a composition comprising one or more vinylidene dimer derived alcohols. The one or more vinylidene dimer derived alcohols are prepared by a process comprising reacting one or more vinylidene dimers with one or more carbonyl-containing compounds, optionally in the presence of a catalyst, under reaction conditions sufficient to produce one or more vinylidene dimer derived alcohols.

This disclosure yet further relates in part to a composition comprising one or more vinylidene dimer derived saturated esters. The one or more vinylidene dimer derived saturated esters are prepared by a process comprising reacting one or more vinylidene dimers with one or more carbonyl-containing compounds, optionally in the presence of a catalyst, under reaction conditions sufficient to produce one or more vinylidene dimer derived alcohols; reacting the one or more vinylidene dimer derived alcohols with one or more acids or anhydrides under reaction conditions sufficient to produce one or more vinylidene dimer derived unsaturated esters; and hydrogenating the one or more vinylidene dimer derived unsaturated esters under reaction conditions sufficient to produce one or more vinylidene dimer derived saturated esters.

This disclosure also relates in part to a composition comprising one or more vinylidene dimer derived saturated esters. The one or more vinylidene dimer derived saturated esters are prepared by a process comprising reacting one or more vinylidene dimers with one or more carbonyl-containing compounds, optionally in the presence of a catalyst, under reaction conditions sufficient to produce one or more vinylidene dimer derived alcohols; hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated esters.

This disclosure further relates in part to a lubricating oil base stock comprising any of the above vinylidene dimer derived saturated ester compositions.

This disclosure yet further relates in part to a lubricating oil comprising a lubricating oil base stock as a major component, and one or more lubricating oil additives, as a minor component. The lubricating oil base stock comprises any of the above vinylidene dimer derived saturated ester compositions.

It has been surprisingly found that vinylidene mPAO chemistry can be leveraged to make 'Guerbet type" alcohols. The carbonyl-ene processes of this disclosure are carried out under reaction conditions sufficient to activate a carbonyl group and scavenge an acidic proton, thereby producing vinylidene dimer derived alcohols. Additionally, value has been surprisingly found in unhydrogenated mPAO chemistry (e.g., mPAO byproducts and utilization of mPAO plants).

Also, it has been surprisingly found that the 'Guerbet type" alcohols derived from vinylidene mPAO chemistry can be used to produce vinylidene dimer derived esters. The vinylidene dimer derived esters are useful as lubricating ester oil base stocks in lubricating oils.

Further objects, features and advantages of the present disclosure will be understood by reference to the following drawings and detailed description.

DETAILED DESCRIPTION

All numerical values within the detailed description and the claims herein are modified by "about" or "approximately" the indicated value, and take into account experimental error and variations that would be expected by a person having ordinaryskill in the art.

In an embodiment, this disclosure relates to the synthesis of 'Guerbet type' branched alcohols from vinylidene mPAO dimer chemistry. These alcohols can be high molecular weight grades up to $C_{16}$-$C_{32}$ carbons. Thus, these alcohols target unique product properties like low volatility and can support chemicals intermediate growth. These alcohols can also be precursors to ester platform for synthetic base stock and plasticizer applications. The carbonyl-ene reaction of formaldehyde ($C_1$-electrophile) with olefins as such or promoted by Lewis acid is a powerful tool for the preparation of various homoallylic alcohols. In a preferred embodiment, mPAO dimer is reacted with formaldehyde to obtain alcohol as shown in the simplified schematic below.

In accordance with this disclosure, vinylidene mPAO chemistry can be leveraged to make 'Guerbet type" alcohols. The processes of this disclosure provide value in unhydrogenated mPAO chemistry (e.g., mPAO byproducts and utilization of mPAO plants).

Further, 'Guerbet type' branched alcohol based products of this disclosure can have better low temperature properties than Oxo alcohol based products. Unique alkyl alcohols can be produced by the processes of this disclosure using various olefins, in particular, vinylidene mPAO dimers. In an embodiment, the process of this disclosure involves activating a carbonyl group and scavenging an acidic proton and utilizes 'atom economy' (i.e., no byproducts).

In an embodiment, this disclosure relates to processes for producing vinylidene dimer derivatives. A double bond terminated alkane as prepared by α-olefin dimerization or ethylene oligomerization (e.g., polyalphaolefin oligomer such as mPAO dimer ($C_6$-$C_{40}$)) is reacted with a carbonyl compound (e.g., paraformaldehyde) to obtain vinylidene dimer derivatives (e.g., vinylidene dimer alcohols).

Illustrative vinylidene dimers useful in the processes of this disclosure include, for example, mPAO dimers ($C_6$-$C_{40}$), and the like.

In an embodiment, the mPAO dimer can be any dimer prepared from any olefin or alpha-olefin using metallocene or other single-site or any Lewis or Bronsted acid, or zeolite or acidic ionic liquid catalyst with terminal double bond. The dimer can be from 1-decene, 1-octene, 1-dodecene, 1-hexene, 1-tetradecene, 1-octadecene or combination of alpha-olefins.

The olefin feed useful in the process of this disclosure can include a light olefinic byproduct fraction including dimers and light fractions from the metallocene-catalyzed PAO oligomerization process. These intermediate light fractions may be generally characterized as $C_{42}$ or lower olefinic distillate fractions that contain a mixture of highly reactive oligomers derived from the original alpha-olefin starting material.

The metallocene-derived intermediate useful as a feed material is produced by the oligomerization of an alpha-olefin feed using a metallocene oligomerization catalyst. The alpha olefin feeds used in this initial oligomerization step are typically alpha-olefin monomers of 4 to 24 carbon atoms, usually 6 to 20 and preferably 8 to 14 carbon atoms. Illustrative alpha olefin feeds include, for example, 1-butene, 1-hexene, 1-octene, 1-decene, 1-dodecene, 1-tetradecene, and the like. The olefins with even carbon numbers are preferred as are the linear alpha-olefins, although it is possible to use branched-chain olefins containing an alkyl substituent at least two carbons away from the terminal double bond.

The initial oligomerization step using a metallocene catalyst can be carried out under the conditions appropriate to the selected alpha-olefin feed and metallocene catalyst. A preferred metallocene-catalyzed alpha-olefin oligomerization process is described in WO 2007/011973, which is incorporated herein by reference in its entirety and to which reference is made for details of feeds, metallocene catalysts, process conditions and characterizations of products.

The dimers useful as feeds in the process of this disclosure possess at least one carbon-carbon unsaturated double bond. The unsaturation is normally more or less centrally located at the junction of the two monomer units making up the dimer as a result of the non-isomerizing polymerization mechanism characteristic of metallocene processes. If the initial metallocene polymerization step uses a single 1-olefin feed to make an alpha-olefin homopolymer, the unsaturation will be centrally located but if two 1-olefin comonomers have been used to form a metallocene copolymer, the location of the double bond may be shifted off center in accordance with the chain lengths of the two comonomers used. In any event, this double bond is 1,2-substituted internal, vinylic or vinylidenic in character. The terminal vinylidene group is represented by the formula $R_aR_bC=CH_2$, referred to as vinyl when the formula is $R_aHC=CH_2$. The amount of unsaturation can be quantitatively measured by bromine number measurement according to ASTM D1159 or equivalent method, or according to proton or carbon-13 NMR. Proton NMR spectroscopic analysis can also differentiate and quantify the types of olefinic unsaturation.

The carbonyl-containing compounds useful as feeds in the processes of this disclosure includes compounds of the formula R—CO—H where R can be aliphatic, cyclic or aromatic group with C1 to C30 carbons. For example, acyclic aliphatic aldehydes can be methanal or formaldehyde, ethanal or acetaldehyde, propanal or propionaldehyde, butanal or butyraldehyde, pentanal or valeraldehyde, 3-methylbutanal, hexanal, heptanal, octanal, decanal, nonanal, undecanal, tridecanal, valeraldehyde, dedecyl aldehyde, lauric aldehyde, and the like.

Illustrative cyclic aldehydes include, for example, cyclohexanecarbaldehyde ($C_6H_{11}CHO$), 3-methylcyclohexanecarbaldehyde, 3,3-dibromocyclopen, and the like.

Illustrative aromatic aldehydes include, for example, benzaldehyde, tolualdehyde, p-nitobenzaldehyde, salicylaldehyde, phenylacetaldehyde, furfural, 3-furancarboxaldehyde, 5-(hydroxymethyl)furfural, 2-thiophenecarboxaldehyde, 3-thiophenecarboxaldehyde, 4-methylthiophene-2-carboxaldehyde, 3-methyl-2-thiophenecarboxaldehyde, tetrahydro-2-furancarboxaldehyde, 4-boro-2-furfural, and the like.

In the above formula, R group can contain a heteroatom such as oxygen, nitrogen or sulfur. Illustrative of such compounds include, for example, 2-chloropentanal, acrolein, crotonaldehyde, glutaldehyde, $CHOCH_2COOH$, 3-oxopropanoic acid, 4-oxopentanal, 3,4-dioxopentanal, 2-methyl-3-oxo-butanol, and the like. Most preferred aldehydes include formaldehyde, paraformaldehyde, acetaldehyde, trioxane, and the like. Aldehydes can be natural, for example, cinnamaldehyde, cilantro, vanillin, and the like. Illustrative of such compounds can also be dialdehydes, for example, glyoxal, malondialdehyde, succindialdehyde, glutaraldehyde, phthalaldehyde, and the like. Other suitable aldehydes include, for example, tiglic aldehyde, undecylenic aldehyde, phenylpropargyl aldehyde, myristicin aldehyde, betaine aldehyde chloride, and the like.

Illustrative cyclic heteroatom containing aldehydes include, for example, 2-thiazolecarboxaldehyde, 5-thiazolecarboxaldehyde, thiazole-4-carboxaldehyde, 4-oxazolecarboxaldehyde, 2-imidazolecarboxaldehyde, 4-imidazolecarboxaldehyde, 3-thiophenecarboxaldehyde, 3-furancarboxaldehyde, furfural, cyclopentane carboxaldehyde, 2-methylpyridine-2-carboxaldehyde, 3-methylpyridine-2-carboxaldehyde, 4-formylphenylboronic acid, cyclohexane carboxaldehyde, 2-cyanobenzaldehyde, 4-formylbenzonitrile, benzothiazole-2-carboxaldehyde, piperonal, phenyl acetaldehyde, 4-methylyhiobenzladehyde, benzo[b]thiophene-2-carboxaldehyde, 2-benzofuran carboxaldehyde, indole-4-carboxaldehyde, indole-3-carboxaldehyde, indole-5-carboxaldehyde, indole-6-carboxaldehyde, indole-7-carboxaldehyde, trans-cinnamaldehyde, 2-quinoline carboxaldehyde, 3-quinoline carboxaldehyde, 4-isoquinoline carboxaldehyde, di-n-butylcetaldehyde, 1-napthaldehyde, and the like.

Illustrative Lewis acid catalysts useful for carbonyl-ene reactions include, for example, metal and metalloid halides conventionally used as Friedel-Crafts catalysts. Suitable examples include $AlCl_3$, $BF_3$, $AlBr_3$, $TiCl_3$, and $TiCl_4$, either as such or with a protic promoter. Other examples include solid Lewis acid catalysts, such as molecular sieves including synthetic or natural zeolites; acid clays; polymeric acidic resins; amorphous solid catalysts, such as silica-alumina; and heteropoly acids, such as the tungsten zirconates, tungsten molybdates, tungsten vanadates, phosphotungstates and molybdotungstovanadogermanates (e.g. $WO_x/ZrO_2$ and $WO_x/MoO_3$). Beside these catalysts, acidic ionic liquid can also be used as catalysts for coupling reactions. Among different catalysts polymeric acidic resins, such as Amberlyst 15, Amberlyst 36 are most preferred. Typically, the amount of acid catalyst used is 0.1 to 30 weight % and preferably 0.2 to 5 weight % based on total weight of the feed.

Illustrative vinylidene dimer alcohols produced by the processes of this disclosure include, for example, long chain branched alcohols such as 3-hexylideneundecan-1-ol, 3-octylideneundecan-1-ol, and the like.

In an embodiment, long chain branched alcohol compositions of this disclosure include, for example, the reaction product of one or more vinylidene dimers and one or more carbonyl-containing compounds.

The composition of this disclosure can be prepared by a process that involves reacting one or more vinylidene dimers with one or more carbonyl-containing compounds, optionally in the presence of a catalyst. The reaction is also carried out under reaction conditions sufficient to produce the composition.

Reaction conditions for the reaction of the vinylidene dimer (e.g., mPAO dimer) with the carbonyl-containing compound (e.g., paraformaldehyde), such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to about 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 48 hours, preferably from about 1 to 36 hours, and more preferably from about 2 to 24 hours.

In accordance with this disclosure, the vinylidene dimer derived alcohols prepared by the carbonyl-ene reaction contain a double bond. Such unsaturated vinylidene dimer derived alcohols can be reacted with appropriate acids to obtain vinylidene dimer derived esters that are unsaturated and contain double bond. The vinylidene dimer derived unsaturated esters can then be hydrogenated to obtain vinylidene dimer derived saturated esters.

Further, in accordance with this disclosure, the vinylidene dimer derived alcohols prepared by carbonyl-ene reaction can be hydrogenated to obtain vinylidene dimer derived saturated branched alcohols. Such vinylidene dimer derived saturated branched alcohols can be reacted with appropriate acids to obtain vinylidene dimer derived esters that are saturated vinylidene dimer derived esters.

Illustrative acids and anhydrides include, for example, aromatic acids, aliphatic acids, glycol ether acids, carboxylic diacids and anhydrides, and the like.

Illustrative aromatic acids useful in the process of this disclosure include, for example, benzoic acid, phenylacetic acid, phenylpropionic acid, phenylbutyric acid, p-tolylacetic acid, xylylacetic acid, tolylpropionic acid, xylylpropionic acid, 4-methoxyphenylacetic acid, methoxyphenylpropionic acid, methoxyphenylbutyric acid, 4-nitrophenylacetic acid, 4-nitrophenylpropionic acid, 4-nitrophenylbutyricacid, xyxylbutyric acid, tolylbutyric acid, and the like.

Illustrative aliphatic acids useful in the process of this disclosure include, for example, valeric acid, isovaleric acid, isobutyric acid, hexanoic acid, heptanoic acid, pentanoic acid, 2-ethylhexanoic acid, octanoic acid, isooctanoic acid, nonanoic acid, isononanoic acid, isotridecanoic acid, tetradecanoic acid, stearic acid, isosteric acid, 2-butylhexanoic acid, 2-butyloctanoic acid, 2-hexyldecanoic acid, 2-hexyloctanoic acid, 2-butylhexanoic acid, 2-heptylundecanoic acid, 2-octyldecanoic acid, 2-butyldecanoic acid, 2-octyldecanoic acid, 2-decyldodecanoic acid, isotridecanoic acid, 2-butyldodacanoic acid, 2-hexyldecacanoic acid, 2-ethylhexanoic acid, and the like.

Illustrative glycol ether acids useful in the process of this disclosure include, for example, methoxyacetic acid, methoxypropionic acid, methoxyethoxyacetic acid, metboxyethoxyethoxyacetic acid, ethoxyacetic acid, ethoxyethoxyacetic acid, ethoxyethoxyethoxyacetic acid, proproxyacetic acid, propoxyethoxyacetic acid, propoxyethoxyetboxyacetic acid, butoxy acetic acid, butoxyethoxyacetic acid, butoxyethoxyethoxyacetic acid, propoxybenzoic acid, and the like.

Illustrative carboxylic diacids useful in the process of this disclosure include, for example, succinic acid, 2-methylsuccinic acid, 2-ethylsuccinic acid, 2-propylsuccinic acid, 2-hexylsuccinic acid, 2-octylsuccinic acid, 2-nonylsuccinic acid, 2-dodecylsuccinic acid, adipic acid, 2-methyladipic acid, 2-ethyladipic acid, 2-propyladipic acid, 2-hexyladipic acid, 2-octyladipic acid, 2-nonyladipic acid, 2-dodecyladipic acid, malonic acid, alkylmalonic acid, azelaic acid, alkylazelaic acid, and the like.

Illustrative carboxylic anhydrides useful in the process of this disclosure include, for example, succinic anhydride, 2-methysuccinic anhydride, 2-ethyl succinic anhydride, 2-propyl succinic anhydride, 2-hexyl succinic anhydride, 2-octylsuccinic anhydride, 2-nonylsuccinic anhydride, 2-dodecyl succinic anhydride, malonic anhydride, alkylmalonic anhydride, and the like.

Reaction conditions for the reaction of the vinylidene dimer alcohol with one or more acids or anhydrides, such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to about 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 48 hours, preferably from about 1 to 36 hours, and more preferably from about 2 to 24 hours.

Illustrative saturated esters produced by the processes of this disclosure include, for example, 3-ethylpentyl hexanoate, 3-ethylpentyl benzoate, 3-hexylundecyl 1-hexanoate, 3-heptyldecyl hexanoate, 3-hexylundecyl benzoate, 3-heptyldecyl benzoate, 3-octyltridecyl hexanoate, 3-octyltridecyl heptanoate, 3-octyltridecyl benzoate, and the like.

Illustrative unsaturated esters produced by the processes of this disclosure include, for example, (Z)-3-ethylpent-3-en-1-yl hexanoate, (Z)-3-ethylpent-3-en-1-yl benzoate, (E)-3-hexylideneundecyl hexanoate, (E)-3-heptyldec-3-en-1-yl hexanoate, (E)-3-hexylideneundecyl benzoate, (E)-3-heptyldec-3-en-1-yl benzoate, (E)-3-octyltridec-3-en-1-yl hexanoate, (E)-3-octylidenetridecyl hexanoate, (E)-3-octylidenetridecyl benzoate, (E)-3-octyltridec-3-en-1-yl benzoate, and the like.

The present disclosure provides a process for producing vinylidene dimer derivatives. The process includes subjecting one or more vinylidene dimers to a carbonyl-ene reaction to obtain a vinylidene derived alcohols. The vinylidene dimers can have a low pour point and low kinematic viscosity compared to alpha olefins and isomerized olefins, making them particularly suitable for applications at low temperature and/or requiring a low viscosity, for instance in applications like additives for lubricating oils and greases, surfactants and PVC plasticizers.

In particular, the $C_6$-$C_{11}$ and $C_{12}$-$C_{18}$ branched alcohols produced by the processes of this disclosure can be used as 'plasticizer alcohols' and 'detergent alcohols'.

This disclosure relates to developing new alcohol platform. This disclosure provides a process for preparing branched alcohols and the uses thereof. Long chain alcohols having about 8 to 32 carbon atoms and their derivatives have considerable commercial importance in a variety of applications. Such applications include, for example, consumer products such as detergents, soaps, personal care products, drug products, as well as industrial products such as surfactants, degreasers, industrial cleaners, and additives for lubricating oils and greases. In addition, the alcohols can be reacted with acids or anhydrides to obtain esters, that can be used as base stocks and PVC plasticizers.

Examples of techniques that can be employed to characterize the compositions formed by the process described above include, but are not limited to, analytical gas chromatography, nuclear magnetic resonance, thermogravimetric analysis (TGA), inductively coupled plasma mass spectrometry, differential scanning calorimetry (DSC), volatility and viscosity measurements.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

EXAMPLES

Example 1

Figure 1:
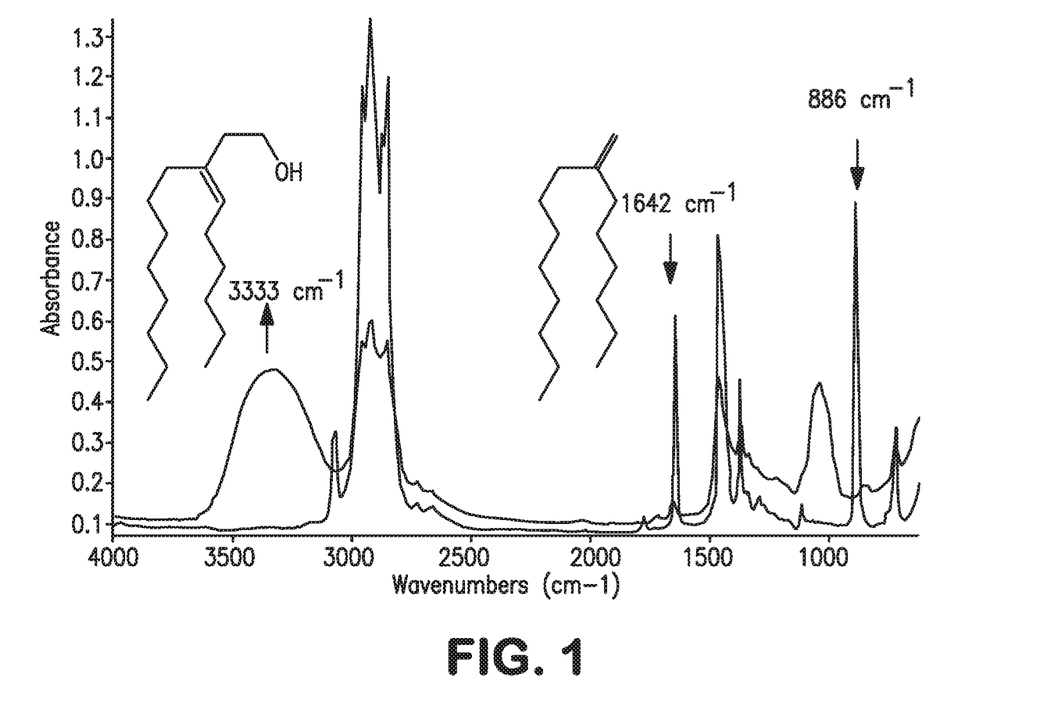
FIG. 1 depicts IR spectra of the C8 mPAO dimer (C16=) and paraformadehyde reacted mPAO dimer product of Example 1.
Figure 2:
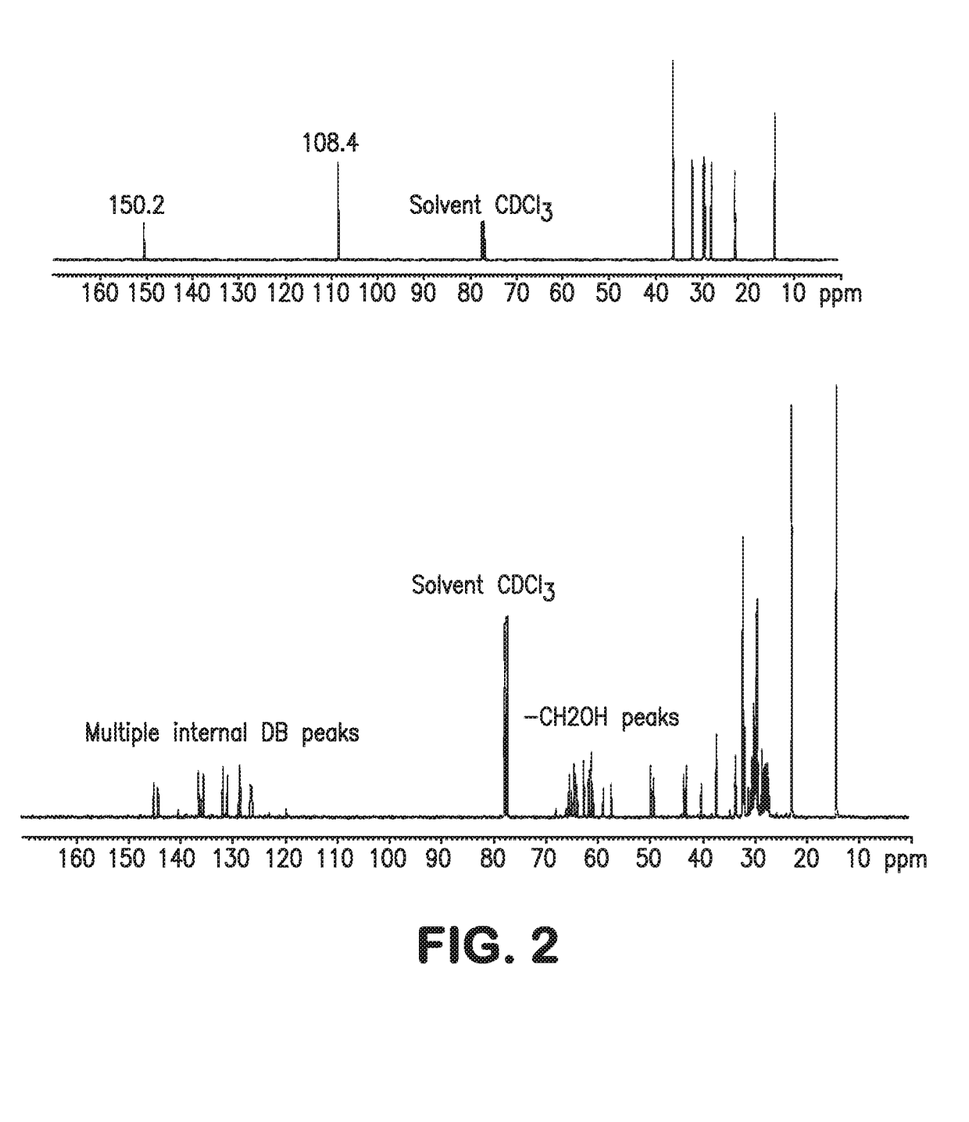
FIG. 2 depicts $^{13}$CNMR spectra of the C8 mPAO dimer (C16=) and paraformadehyde reacted mPAO dimer product of Example 1.

Carbonyl-Ene Reaction of $C_8$ Dimer (C16=) with Paraformadehyde in Presence of Dimethylaluminum Chloride mPAO $C_{16}$ dimer (10.0 g, 0.0446 moles, MW: 224.43), paraformaldehyde (2.68 g, 0.0892 moles, MW: 30.03) was dissolved in 50 ml of dry dichloromethane in 250 ml round bottom flasks under nitrogen. Slowly added (6.19 g, 0.0669 mole, MW: 92.5) dimethylaluminum chloride in 15 ml methylene chloride at 5-10° C. and stirred the solution for 18 hours at room temperature. Stop the reaction by adding saturated aqueous $NaHCO_3$ at 10-15° C. The resulting suspension filtered through celite and washed with 10 ml of 10% HCl (1×75 ml) and water (1×75 ml). The organic layer is dried over anhydrous $MgSO_4$. The solvent was removed by rotavapor at 50° C. and high boiling components by air bath oven at 180° C. under 2 mm vacuum for 2 hours to obtain the product. Yields: 9.5 g (about 84%). Both NMR and IR analysis was suggested the formation of alcohol mixtures. IR spectra of the mPAO dimer and paraformadehyde reacted mPAO dimer product is shown in FIG. 1. IR: 3346, 2955, 2925, 2855, 1466, 1377, 1045, 721. The product $^{13}C$ NMR showed the disappearance of $C_{16}$ dimer terminal vinylidene peaks at 150.17 and 108.45 ppm and new set of methylene attached to hydroxyl group peaks appeared at 65.75-57.11 ppm as shown in FIG. 2.

Example 2

Esterification of Alcohol Mixture Obtained from the Example 1 with Hexanoic Acid in Presence of Titanium (VI) Isopropoxide The alcohol mixture obtained from the Example 1 (5 g, 0.0197 mol, MW: 254.45), hexanoic acid (4.57 g 0.0393 mol, MW: 116.16) and titanium (IV) isopropoxide (0.560 g, 0.00197 mol, MW: 284.22) were mixed 100 ml toluene in 250 ml two necked round bottom flask along with a dean-stark apparatus. Then solution was reflux for overnight (18 h). In 18 hours, about 1-1.5 ml water was collected in the trap. Toluene was removed by simple distillation at 75° C. and excess of hexanoic acid was distilled with air bath oven at 180° C. under high vacuum and flask chromatography with hexane/toluene (50/50) to obtain the product. Yields: 5.2 g. The IR analysis was suggested the formation of mono ester. The product IR showed the disappearance of hydroxyl group peaks at 3334 cm$^{-1}$ and new set of peaks are developed at 1739 cm$^{-1}$, 1560 cm$^{-1}$, 1245 cm$^{-1}$, 1168 cm$^{-1}$ and 766 cm$^{-1}$ which are corresponding to ester functional group.

Example 3

Esterification of Alcohol Mixture Obtained from the Example 1 with Benzoic Acid in Presence of Titanium (VI) Isopropoxide The alcohol mixture obtained from the Example 1 (5 g, 0.0197 mol, MW: 254.45), benzoic acid (3.61 g 0.00296 mol, MW: 116.16) and PTSA (0.750 g, 0.00394 mol, MW: 190.22) were mixed 75 ml toluene in 250 ml two necked round bottom flask along with a dean-stark apparatus. Then solution was reflux for overnight (18 h). In 18 hours, about 1-1.5 ml water was collected in the trap. Toluene was removed by simple distillation at 75° C. and excess of alcohol was distilled with air bath oven at 180° C. under high vacuum and flask chromatography with hexane/toluene (50/50) to obtain the product. The IR analysis was suggested the formation of mono ester. Yields: 5.2 g (73%). The product IR showed the disappearance of hydroxyl group peaks at 3334 cm$^{-1}$ and new set of peaks are developed at 1724.76 cm$^{-1}$, 1466 cm$^{-1}$, 1377 cm$^{-1}$, 1271 cm$^{-1}$ and 722 cm$^{-1}$ which are corresponding to ester functional group.

Example 4

Lube Properties

The lube properties of the products of Examples 2 and 3 were evaluated. The kinematic viscosity (Kv) of the liquid product was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The product volatility was measured using thermogravimetric analysis (TGA) based Noack. These fluids were evaluated as Group V base stocks and the results are shown below.

| Base Stock # | Kinematic Viscosity at 100° C. | Kinematic Viscosity at 40° C. | Viscosity Index | Noack Volatility (TGA) |
|---|---|---|---|---|
| Example 2 | 3.56 | 14.0 | 140 | 18.2 |
| Example 3 | 8.73 | 105.3 | 105 | 9.1 |

Example 5

Carbonyl-ene Reactions of Olefins with Paraformaldehyde

2-Methyl-2-heptene (I) was reacted with paraformaldehyde using a combined system of boron trifluoride and molecular sieve 4 A at −5° C. The major isolated product after column chromatography and characterization by GCMS, NMR and IR was found to be the mono-alcohol adduct [2-butyl-3-methyl-3-buten-1-ol] (about 80% isolated yield) and the second major product (about 15%, isolated yield) was the diol functionalized olefin (III). Similarly, 2-methyl-2-heptene (I) was reacted with paraformaldehyde using dimethyl aluminum chloride, which is a mild Lewis acid, and a proton scavenger to catalyze the ene reaction at room temperature. The major isolated product was found to be the mono-alcohol adduct [2-butyl-3-methyl-3-buten-1-ol]. The processes potentially can be carried out using inexpensive formaldehyde without a promoter.

The major isolated product after column chromatography and by characterization by GCMS, NMR and IR was found to be the mono-alcohol adduct [2-butyl-3-methyl-3-buten-1-ol (II)] (about 80% isolated yield). The IR spectra showed that the double bond peak of the starting olefin at 1673 $cm^{-1}$ shifts to the new vinylidene peak at 1645 $cm^{-1}$ for product (II) and at 1641 $cm^{-1}$ for product (III). There was also a large peak at 3300 $cm^{-1}$ due to hydroxyl group appeared in both the products.

The NMR spectra were acquired with the 5 mm switchable probe on the Varian UnityPlus 500. The samples were prepared in chloroform-d, with relaxation agent —Cr(acac)$_3$-added to the carbon samples to accelerate data acquisition. Free induction decay of 288 and 12000 co-added transients were acquired for the carbon spectrum of the starting olefin and product, respectively, while 20 scans sufficed for the proton run. All spectra were acquired at a temperature of 30° C.

The proton and carbon spectrum spectra of the starting olefin both confirm structure. The $^{13}$C NMR spectrum of the starting 2-methyl-2-heptene showed typical trisubstituted olefin peaks at 131.1 and 125.1 ppm. The carbon spectrum of the carbonyl-ene reaction product (II) indicates the proposed 2-proenyl-1-hexanol to be the dominant product. The $^{13}$C NMR showed all 9 carbon peaks in the spectrum with the disappearance of trisubstituted olefin peaks at 131.1 and 125.1 ppm and new olefin peaks appearing at 145.6 and 113.4 ppm corresponding to terminal vinylidene resonances. The product also showed the methylene attached to hydroxyl resonance at 64.4 ppm and tertiary carbon at 50.2 ppm. The second major product (about 15%, isolated yield) was the diol functionalized olefin (III). The carbon spectrum of the product (III) showed 10 carbon peaks with the new olefin peaks at 147.3 and 113.4 ppm. The spectrum also showed the methylene resonance at 66.2 ppm and 613 ppm due to two OH attached carbons and 48.7 ppm due to tertiary carbon with —$CH_2OH$ group. This suggests that there was a double addition of formaldehyde to the olefin molecule. The mass spectra of the product (II) and (III) showed m/e at 142 and 172 due to mono- and bi-adducts respectively.

Example 6

Carbonyl-ene Reaction of 2-methyl-2-heptene with Paraformaldehyde using a Combined System of Boron Trifluoride and Molecular Sieve 4 A A mixture of 2.28 g $BF_3.OEt_2$ (FW 141.93, 0.016 moles) and molecular sieves 4 A (15.0 g) in $CH_2Cl_2$ (50 ml) was stirred at −5° C. A solution of 1.5 g 2-methyl-2-heptene (FW 112.22, 0.013 moles) and 0.40 g paraformaldehyde (FW 30.03, 0.013 moles) were added and the reaction mixture was stirred for 3 hours. To the reaction mixture was added saturated aqueous $NaHCO_3$ to quench the reaction, and the mixture was filtered through a Celite pad. The organic layer was separated, washed with saturated aqueous $NaHCO_3$ and dried over $Na_2SO_4$. After filtration and evaporation under reduced pressure, the crude product was chromatographed on silica gel. The major product (I) was obtained (80%) from ethyl acetate solvent and remaining isolated product (II) was obtained from acetone solvent.

Example 7

Carbonyl-ene Reaction of 2-methyl-2-heptene with Paraformaldehyde using Dimethylaluminum Chloride A mixture of 1.0 g 2-methyl-2-heptene (FW 112.22, 0.0082 moles) and 0.2457 g paraformaldehyde (FW 30.03, 0.0082 moles) were added to $CH_2Cl_2$ (30 ml). 1.2365 g (0.01337 moles) of dimethylaluminum chloride was then added and the reaction mixture was stirred for 18 hours at room temperature. The solution was added to 10 ml of aqueous $NaHCO_3$, poured into 50 ml ether. 10 ml of a 10% solution of aqueous HCl was added to dissolve the aluminum salts. The $CH_2Cl_2$ layer was then separated, washed with 10% sodium hydroxide, then dried over $MgSO_4$. The solvent was removed to obtain the product (about 95% isolated yield). The IR and $^{13}$C NMR spectra of the product suggest to the mono-alcohol adduct [2-butyl-3-methyl-3-buten-1-ol (II)].

PCT and EP Clauses:

1. A process for producing a composition comprising one or more vinylidene dimer derivatives, said process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols.

2. A process for producing a composition comprising one or more vinylidene dimer derivatives, said process comprising: subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; reacting the one or more vinylidene dimer derived alcohols with one or more acids or anhydrides under reaction conditions sufficient to produce one or more vinylidene dimer derived unsaturated esters; and hydrogenating the one or more vinylidene dimer derived unsaturated esters under reaction conditions sufficient to produce one or more vinylidene dimer derived saturated esters.

3. A process for producing a composition comprising one or more vinylidene dimer derivatives, said process comprising: subjecting one or more vinylidene dimers and one or more carbonyl-containing compounds to a carbonyl-ene reaction, optionally in the presence of a catalyst, under reaction conditions sufficient to produce one or more vinylidene dimer derived alcohols;

hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated esters.

4. The process of clauses 1 through 3 wherein the one or more vinylidene dimers are selected from mPAO dimers ($C_6$-$C_{40}$); the one or more carbonyl-containing compounds are selected from aldehydes; and the at least one catalyst is selected from Lewis acids.

5. The process of clauses 1 through 3 wherein the Lewis acids are selected from metal halides, metalloid halides, molecular sieves, and combinations thereof.

6. The process of clauses 1 through 3 which is carried out under reaction conditions sufficient to activate a carbonyl group and scavenge an acidic proton, to produce said one or more vinylidene dimer derived alcohols.

7. The process of clauses 1 through 3 wherein said one or more vinylidene dimer derived alcohols comprise one or more branched alcohols having about 8 to about 32 carbon atoms.

8. A composition comprising one or more vinylidene dimer derived alcohols, said one or more vinylidene dimer derived alcohols prepared by a process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols.

9. A composition comprising one or more vinylidene dimer derived saturated esters, said one or more vinylidene dimer derived saturated esters prepared by a process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; reacting the one or more vinylidene dimer derived alcohols with one or more acids or anhydrides under reaction conditions sufficient to produce one or more vinylidene dimer derived unsaturated esters; and hydrogenating the one or more vinylidene dimer derived unsaturated esters under reaction conditions sufficient to produce one or more vinylidene dimer derived saturated esters.

10. A composition comprising one or more vinylidene dimer derived saturated esters, said one or more vinylidene dimer derived saturated esters prepared by a process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated esters.

11. The composition of clauses 8 through 10 wherein the one or more vinylidene dimers are selected from mPAO dimers ($C_6$-$C_{40}$); the one or more carbonyl-containing compounds are selected from aldehydes; and the at least one catalyst is selected from Lewis acids.

12. The composition of clauses 8 through 10 wherein the Lewis acids are selected from metal halides, metalloid halides, molecular sieves, and combinations thereof.

13. The composition of clauses 8 through 10 which is carried out under reaction conditions sufficient to activate a carbonyl group and scavenge an acidic proton, to produce said one or more vinylidene dimer derived alcohols.

14. The composition of clauses 8 through 10 wherein said one or more vinylidene dimer derived alcohols comprise one or more branched alcohols having about 8 to about 32 carbon atoms.

15. A lubricating oil base stock comprising the composition of clauses 9 or 10.

16. A lubricating oil comprising a lubricating oil base stock as a major component, and one or more lubricating oil additives, as a minor component; wherein the lubricating oil base stock comprises the composition of clauses 9 or 10.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

The invention claimed is:

1. A process for producing a composition comprising one or more vinylidene dimer derivatives, said process comprising reacting one or more vinylidene dimers with one or more carbonyl-containing compounds, optionally in the presence of a catalyst, under reaction conditions sufficient to produce one or more vinylidene dimer derived alcohols; hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated monoesters.

2. A lubricating oil comprising a lubricating oil base stock as a major component, and one or more lubricating oil additives, as a minor component wherein the lubricating oil base stock comprises a composition comprising one or more vinylidene dimer derived saturated monoesters, said one or more vinylidene dimer derived saturated esters prepared by a process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; reacting the one or more vinylidene dimer derived alcohols with one or more acids or anhydrides under reaction conditions sufficient to produce one or more vinylidene dimer derived unsaturated esters; and hydrogenating the one or more vinylidene dimer derived unsaturated esters under reaction conditions sufficient to produce one or more vinylidene dimer derived saturated esters.

3. A lubricating oil comprising a lubricating oil base stock as a major component, and one or more lubricating oil additives, as a minor component wherein the lubricating oil base stock comprises a composition comprising one or more vinylidene dimer derived saturated monoesters, said one or more vinylidene dimer derived saturated esters prepared by a process comprising subjecting one or more vinylidene dimers and one or more carbonyl-containing compounds to a carbonyl-ene reaction, optionally in the presence of a catalyst, under reaction conditions sufficient to produce one or more vinylidene dimer derived alcohols; hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated esters.

4. A lubricating oil comprising a lubricating oil base stock as a major component, and one or more lubricating oil additives, as a minor component wherein the lubricating oil base stock comprises a composition comprising one or more vinylidene dimer derived saturated monoesters, said one or more vinylidene dimer derived saturated esters prepared by a process comprising reacting one or more vinylidene dimers with one or more carbonyl-containing compounds, optionally in the presence of a catalyst, under reaction conditions sufficient to produce one or more vinylidene dimer derived alcohols; reacting the one or more vinylidene dimer derived alcohols with one or more acids or anhydrides under reaction conditions sufficient to produce one or more vinylidene dimer derived unsaturated esters; and hydrogenating the one or more vinylidene dimer derived unsaturated esters under reaction conditions sufficient to produce one or more vinylidene dimer derived saturated esters.

5. A lubricating oil comprising a lubricating oil base stock as a major component, and one or more lubricating oil additives, as a minor component wherein the lubricating oil base stock comprises a composition comprising one or more vinylidene dimer derived saturated monoesters, said one or more vinylidene dimer derived saturated esters prepared by a process comprising reacting one or more vinylidene dimers with one or more carbonyl-containing compounds, optionally in the presence of a catalyst, under reaction conditions sufficient to produce one or more vinylidene dimer derived alcohols; hydrogenating the one or more vinylidene dimer derived alcohols under reaction conditions sufficient to produce one or more vinylidene dimer derived saturated alcohols; and reacting the one or more vinylidene dimer derived saturated alcohols with one or more acids or anhydrides under reaction conditions sufficient to produce one or more vinylidene dimer derived saturated esters.

6. A composition comprising:
one or more vinylidene dimer derived monoesters, wherein the composition comprises one or more monoesters selected from:

* * * * *